United States Patent
Howard et al.

(10) Patent No.: US 6,274,161 B1
(45) Date of Patent: Aug. 14, 2001

(54) COMPOSITIONS CONTAINING CREATINE IN SUSPENSION

(75) Inventors: Alan N Howard, Cambridge; Roger C Harris, Newmarket, both of (GB)

(73) Assignee: The Howard Foundation, Cambridge (GB)

( * ) Notice: Subject to any disclaimer, the term of this patent is extended or adjusted under 35 U.S.C. 154(b) by 0 days.

(21) Appl. No.: 09/419,922

(22) Filed: Oct. 18, 1999

Related U.S. Application Data

(63) Continuation-in-part of application No. 09/324,119, filed on Jun. 2, 1999, now Pat. No. 6,168,802, which is a continuation-in-part of application No. 08/866,517, filed on May 30, 1997, now Pat. No. 5,968,544.

(30) Foreign Application Priority Data

May 31, 1996  (GB) .................................................. 9611356

(51) Int. Cl.⁷ ..................................................... A61K 9/10
(52) U.S. Cl. .......................... 424/439; 424/484; 424/488; 514/773; 514/777; 514/783; 514/970; 514/944
(58) Field of Search ..................................... 424/484, 485, 424/488, 439

(56) References Cited

U.S. PATENT DOCUMENTS

| | | | |
|---|---|---|---|
| 3,615,600 | 10/1971 | Tonsbeek | 99/140 |
| 4,464,409 | 8/1984 | Rooij | 426/536 |
| 4,647,453 | 3/1987 | Meisner | 424/54 |
| 4,772,591 | 9/1988 | Meisner | 514/62 |
| 5,773,473 | 6/1998 | Green et al. | 514/565 |
| 5,908,864 | 6/1999 | Casey | 514/564 |
| 6,075,031 | * 6/2000 | Kaddurah-Daouk et al. | 514/275 |

FOREIGN PATENT DOCUMENTS

| | | |
|---|---|---|
| 59025663 | 2/1984 | (EP) . |
| 0669083 | 2/1995 | (EP) . |
| 2 313 544 | 12/1997 | (GB) . |
| 50087771 | 9/1996 | (JP) . |
| WO94/02127 | 2/1994 | (WO) . |
| WO94/15488 | 7/1994 | (WO) . |
| WO94/17794 | 8/1994 | (WO) . |
| WO96/04240 | 2/1996 | (WO) . |
| WO 96/14063 | 5/1996 | (WO) . |
| WO96/36348 | 11/1996 | (WO) . |
| 98/53704 | 12/1998 | (WO) . |

OTHER PUBLICATIONS

PMI Nutrition International, Lab Diet 5001, 1996.*

* cited by examiner

*Primary Examiner*—James M. Spear
(74) *Attorney, Agent, or Firm*—Pillsbury Winthrop LLP

(57) ABSTRACT

Disclosed is a composition for human consumption comprising creatine suspended in an edible supporting matrix, a method of making the composition, and a method of stably storing creatine-containing foodstuffs at ambient temperature.

14 Claims, No Drawings

COMPOSITIONS CONTAINING CREATINE IN SUSPENSION

This is a continuation-in-part of Ser. No. 09/324,119, filed Jun. 2, 1999, now U.S. Pat. No. 6,168,802, which is a continuation-in-part of Ser. No. 08/866,517, filed May 30, 1997, now U.S. Pat. No. 5,968,544.

FIELD OF THE INVENTION

This invention relates to compositions for human consumption comprising creatine in suspension and to a method of providing stable creatine containing compositions.

BACKGROUND TO THE INVENTION

In the last few years there has been considerable interest among athletes in creatine, which occurs abundantly in skeletal muscle. Creatine plays a pivotal role in the regulation and homeostasis of skeletal muscle energy metabolism and it is now generally accepted that the maintenance of phospho creatine availability is important to the continuation of muscle force production. Although creatine synthesis occurs in the liver, kidney and pancreas it has been known for sometime that the oral ingestion of creatine will add to the whole body creatine pool, and it has been shown that the ingestion of 20 to 30 g creatine per day for several days can lead to a greater than 20% increase in human skeletal muscle total creatine content. Thus, WO94/02127 discloses the administration of creatine in amounts of at least 15 g (or 0.2–0.4 g/kg body weight) per day, for at least 2 days, for increasing muscular strength.

In fact, it was subsequently found that after several days of supplementation (20 g per day) with creatine in order to attain saturation, thereafter it takes no more than 2 to 3 g per day to maintain the saturation of body stores. Creatine supplementation in an appropriate dose can provide improvements to athletes involved in explosive events, which include all events lasting from a few seconds to a few minutes (such as sprinting, swimming, weight-lifting etc). Endurance performance in events lasting longer than about 30 minutes appears to be unaffected by creatine supplementation. Creatine is a normal food component and is not a drug and its use is not contrary to official regulations. The biggest benefits of supplementation can be experienced by the elderly, vegetarians or those who eat no meat or fish since these people tend to have low muscle creatine content.

Aloe Vera (*Aloe barbadensis*) is a member of the lily family and is a cactus like succulent plant that grows in warm frost free climates. Central American Mexican Indians used Aloe Vera for centuries as a remedy for burns, to prevent blisters, peptic and duodenal ulcers and all types of stomach and intestinal disorders, kidney infections, topical and gastric ulcers as well as to promote longevity. Today Aloe Vera is becoming very popular and its benefits are scientifically recognized.

The main use of Aloe Vera in the past has been to prevent inflammations, particularly to the skin, especially after burns, but there are many other uses. Experiments and research studies have shown that after using Aloe Vera juice, the output of the digestive enzymes and the bacterial population of the intestines are improved. Thus there has been an increasing interest in Aloe Vera as a medicament to be taken orally as people become more acquainted with its medicinal properties.

Among the several methods of presentation, there is a growing use of Aloe Vera in soft drinks which are fruit flavored, and these are quite palatable. The inclusion of creatine in a soft drink would be highly desirable because the Aloe Vera drink would be much more beneficial to health than an unsupplemented ordinary fruit drink.

Aloe Vera juice is acidic (commonly about pH3). It is well known that creatine is unstable in aqueous solutions at acid or neutral pH, and is converted into the related compound creatinine. This is highly significant as creatine has no muscle performance-enhancing effect and is excreted from the human body as a waste product in urine. In view of the foregoing, EP 0 669 083 teaches that aqueous drinks for human consumption comprising creatine must be weakly alkaline, in order to prevent the conversion of creatine into creatinine, and this has become the generally accepted opinion.

Furthermore, creatine has been used in the past only for the preparation of products with a meaty or savory flavor. For instance, Tonsheek (U.S. Pat. No. 3,615,600) discloses and is concerned with artificial flavoring mixtures which can impart a meaty flavor to foods. Similary de Rooji (U.S. Pat. No. 4,464,409) is concerned with meat flavoring. Yamazaki (JP-A-59035663) prepares a meat flavor by heating a mixture comprising creatine at pH 5.0–7.0 at temperature of 80–130° C. for 30–120 minutes. Under these conditions most of the creatine would be converted to creatinine.

It would be a great advantage to present a composition for human consumption, in which the creatine therein was substantially stable, even at acidic pH and at ambient temperatures.

SUMMARY OF THE INVENTION

In a first aspect the invention provides a composition for human consumption comprising creatine suspended in an edible supporting matrix. The term "suspended" is intended to mean that compositions in accordance with the invention comprise creatine in solid form (e.g. as crystals, power or the like), distributed within an edible viscous liquid or semi-liquid, or a solid, supporting matrix, typically such that settling (under the influence of gravity) of the solid creatine is inhibited or prevented.

The creatine content of the composition may be present as any active form of creatine (e.g. creatine phosphate), but creatine monohydrate is found particularly convenient as a source of creatine. The creatine content of the composition is preferably subjected to a micronization process (e.g. crushing, pulverizing, powdering and the like) prior to incorporation into the matrix, so that the resulting composition is not unacceptably "gritty" in texture.

The composition may be provided in solid, liquid or semi-liquid form (e.g. as a drink, soup or yogurt).

Preferably the creatine will be distributed substantially evenly throughout the supporting matrix (by homogenizing in some manner e.g. by stirring, blending and the like), which may be accomplished manually (e.g. by the consumer) and/or mechanically at the time the composition is prepared.

Conveniently the supporting matrix is a recognised foodstuff, such that a composition in accordance with the invention may take the form of an otherwise conventional foodstuff, supplemented with creatine, such that solid creatine becomes suspended in the foodstuff. Examples of foodstuffs which may represent suitable supporting matrices for the composition of the invention include spreadable solids such as dairy or cheese spreads, margarines, caviar (mainly lump fish caviar) spread, and other fish pastes and spreads (eg. buckling paste i.e. a paste made from smoked baltic herring) meat spreads, and the like. Other convenient supporting matrices are those comprising sugars or other carbohydrates, such as liquid ("runny") or solid ("set") honey, molasses, syrup (e.g. corn syrup, glucose syrup), treacle or "Maxim Energy Gel"™.

If desired, the viscosity of the edible matrix and/or the composition as a whole, may be increased by the addition of viscosifiers, gelling agents and the like. Such components are well-known in the food industry and include, for example, plant-derived polysaccharides, gums and the like such as galactomannans, dextrans, guar gum, locust bean gum and so on.

Indeed, such viscosifiers, gels and the like may form the supporting matrix, if desired. One preferred edible matrix comprises a gel prepared from concentrated Aloe Vera extract: a smooth creamy paste (suitable for packaging in a squeezable tube) may be prepared by mixing 5 gms of creatine with 20 mls of a concentrated Aloe Vera gel (such as that obtainable from Aloe Commodities Int. Inc., Farmers Branch, Tex. 75234).

The present inventors have previously found that the conversion of creatine to creatinine in acidic aqueous solutions can be markedly inhibited by storage of creatine-containing solutions below ambient temperature. The inventors have now found that, by providing creatine in the form of a suspension, rather than in solution, conversion to creatinine (even in an acidic composition) can be greatly inhibited or even substantially prevented even at ambient (i.e. 20–25° C.) temperature. Thus, in some embodiments the composition as a whole (and/or the supporting matrix in isolation) may conveniently be selected to be acidic (i.e. have a pH below 7.0), without significantly adversely affecting the stability of the creatine content of the composition. In particular the composition desirably has a pH between 2.5 and 6.5, preferably between 3.0 and 6.0. Typically the composition has a pH in the range 3.5–5.5 which, to the human palate, has a refreshingly sharp taste without being too acidic.

Compositions in accordance with the invention are substantially stable so that creatine may be presented in acidic formulations, contrary to the teaching of the art, in physiologically useful amounts, even following storage for prolonged periods at ambient temperature. A physiologically useful amount of creatine is an amount sufficient to cause a measurable increase in the creatine content of the tissues of a subject following repeated consumption of the composition, relative to an initial baseline level.

The term "substantially stable" is herein defined as referring to a composition in which at least 75% of the original creatine in the composition is unchanged into creatinine for a period of at least 7 days' storage at ambient (20–25° C.) temperature. Desirably the composition will be sufficiently stable that 75% of the creatine remains following a period of at least 31 days', more preferably 45 days', and most preferably at least 73 days' storage at ambient temperature.

The composition may comprise one or more further components to improve its palatability, stability, flavor or nutritive quality. These further components may include electrolytes, as already mentioned above, or may be selected from the group consisting of: vitamins, lipids, carbohydrates, amino acids, trace elements, colorings, flavors, artificial sweeteners, natural health improving substances, anti-oxidants, stabilizers, preservatives, and buffers. The composition may be unflavored or where the edible matrix is a recognised foodstuff (e.g. honey or syrup), the composition may have the normal flavor of the matrix. Alternatively, flavoring may be added (e.g. fruit, cheese or fish flavor).

Vitamins may be included with advantage in the composition of the invention. The following vitamins may be added in amounts which range from 20 to 100% of their recommended daily allowance (RDA). The following are typical of those which are useful: vitamin E, vitamin C, thiamin, riboflavin, niacin, vitamin B6, folacin, vitamin B12, biotin, and pantothenic acid.

In some cases a lipid component may be desirable. The carbohydrate content (if any) or the composition may be present as starch (particularly soluble starch) and/or sugars. The sugars which may be present in the composition include glucose, fructose, sucrose, and maltrose.

Artificial sweeteners which can be used include Aspartame, Acesulfam K, Saccharin and Cyclamate. Almost any desired flavoring can be added, most preferably fruity flavors such as berry, lemon, orange, papaya and grapefruit. Citric acid may also be used as an acidulant and citrate (e.g. sodium citrate) as a buffering agent. Also other natural health improving substances may be added in physiologically active amounts. The following are typical of those which are useful: Pan D'Arco tea, Ginseng, Suma tea, Ginkgo, bee pollen, myrrh.

Preservatives can be provided typically by potassium benzoate and/or potassium sorbate.

Coloring can be provided, typically by using a cold water soluble colorant such as beta-carotene. Other suitable colorings will be apparent to those skilled in the art.

A clouding agent may be included in the composition, if desired, to improve the appearance of the composition.

The mineral and trace elements can also be added in any type or form which is suitable for human consumption. It is convenient to provide the calcium and potassium in the form of their gluconates, phosphates or hydrogen phosphates, and magnesium as the oxide or carbonate, chromium as chromium picolmate, selenium as sodium selenite or selenate, and zinc as zinc gluconate. Typically the amounts are: sodium at 400 mg/liter, calcium at 100 mg/liter, chloride at 600 mg/liter, potassium at 200 mg/liter, magnesium at 75 mg/liter and phosphorus at 50 mg/liter, chromium at 125 µg/liter, selenium at 125 µg/liter and zinc at 15 mg/liter.

The amount of creatine per liter or per Kg of prepared composition may range from 0.5 to 30 g, with a preferred content of about 12 g per liter. The normal serving size is in the range 250–330 ml. providing about 2–5 g (preferably about 3 g) of creatine. During the first 4 days of creatine supplementation the recommended consumption is 1.5 liters per day divided in 4 or 5 parts per day to achieve creatine saturation. This is followed by 1 serving of 250 ml per day containing about 3 g of creatine to provide a maintenance level of creatine.

In a second aspect the invention provides a method of preparing a creatine containing composition for human consumption in which the creatine is substantially stable, the method comprising the steps of providing creatine in solid form; and mixing the solid creatine with an edible supporting matrix so as to distribute the solid creatine within the supporting matrix. The method typically will comprise the further step of packaging the composition. The composition may be packaged in any of a number of conventional packages (e.g. jars, tins, plastic containers, pots, squeezable tubes and the like).

Advantageously, performance of the method of the second aspect will result in a composition in accordance with the first aspect defined above.

In a third aspect the invention provides a method of storing creatine in stable form, the method comprising the steps of providing creatine in solid form; mixing the solid creatine with an edible supporting matrix so as to suspend the creatine therein, and storing the suspended creatine at ambient temperature.

EXAMPLE 1

Four supporting matrices were tested for their suitability for used in the present invention: Sainsbury's liquid honey; Sainsbury's solid honey, Maxim Energy Gel™; and Tate and Lyle Golden Syrup. The Sainsbury's honey and Tate and Lyle syrup are representative of other products of this type. Maxim Energy Gel™ is available from Prinsen BV (Helmond, The Netherlands) and comprises glucose syrup, water, citric acid, flavorings and carotene. Typical composition (per 100 gms) is: carbohydrate 77.6 gm; vitamin B1 0.5 mg; trace amounts of protein; and water to 100 gms.

Experimental Protocol

1. The pH of each matrix was determined by dissolving 11 g in 50 ml distilled water and determining the pH of the resulting solution with a pH meter.
2. 4 g of creatine monohydrate was well mixed and suspended in 40 g of each matrix to give a concentration of 90.9 g/kg of mixture.
3. The mixtures were stored in a dark cabinet at ambient temperature (22.5–23.5° C.) in a laboratory.
4. –3 g of mixture were sampled after 0, 14, 31, 45 and 73 days and stored frozen at –30° C. until analysed.
5. Each sample was dissolved in 500 ml of distilled water and the creatine concentration was determined by the method of Harris et al, (1974 Scand. J. Clin. Lab. Invest. 33, 109–120). Briefly, the assay was performed in the presence of (final concentration) 100 mM tri-ethanolamine buffer pH 8.5; 10 mM magnesium acetate; 1 mM EDTA; 30 mM KCl; 1 mM phosphoenolpyruvate (PEP); 2 mM adenosinetriphosphate (ATP); 0.18 mM nicotinamide-adenine-dinucleotide/reduced form (NADH); creatine kinase (CK); pyruvate kinase (PK), and lactate dehydrogenase (LDH). The concentration of creatine was determined from the oxidation of NADH measured spectrophotometrically at 340 nm.

CK: Cr+ATP →PCr+ADP

PK: ADP+PEP →ATP+Pyruvate

LDH: Pyruvate+NADH→Lactate+NAD

6. The results of the analyses are shown in Tables 1–4 below.

TABLE 1

|  | pH | Day | Abs1 | Abs2 | ΔAbs | g/500 ml | g/kg suspension |
|---|---|---|---|---|---|---|---|
| liquid honey | 3.86 |  |  |  |  |  |  |
|  |  |  | 0.835 | 0.862 |  |  |  |
|  |  | 0 | 0.836 | 0.367 | 0.496 | 2.90 | 91.0 |
|  |  | 14 | 0.837 | 0.342 | 0.522 | 3.12 | 89.0 |
|  |  | 31 | 0.837 | 0.346 | 0.518 | 3.10 | 88.9 |
|  |  | 45 | 0.836 | 0.315 | 0.548 | 3.29 | 88.6 |
|  |  | 73 | 0.836 | 0.313 | 0.550 | 3.20 | 91.5 |

TABLE 2

|  | pH | Day | Abs1 | Abs2 | ΔAbs | g/500 ml | g/kg suspension |
|---|---|---|---|---|---|---|---|
| Solid honey | 3.87 |  |  |  |  |  |  |
|  |  |  | 0.830 | 0.836 |  |  |  |
|  |  | 0 | 0.832 | 0.349 | 0.489 | 2.87 | 90.7 |
|  |  | 14 | 0.831 | 0.301 | 0.536 | 3.16 | 90.3 |
|  |  | 31 | 0.832 | 0.267 | 0.571 | 3.35 | 90.7 |
|  |  | 45 | 0.830 | 0.297 | 0.539 | 3.19 | 89.9 |
|  |  | 73 | 0.831 | 0.286 | 0.551 | 3.31 | 88.6 |

TABLE 3

|  | pH | Day | Abs1 | Abs2 | ΔAbs | g/500 ml | g/kg suspension |
|---|---|---|---|---|---|---|---|
| Maxim gel | 2.05 |  |  |  |  |  |  |
|  |  |  | 0.834 | 0.838 |  |  |  |
|  |  | 0 | 0.834 | 0.439 | 0.399 |  | 91.5 |
|  |  | 14 | 0.835 | 0.324 | 0.515 |  | 90.1 |
|  |  | 31 | 0.835 | 0.336 | 0.503 |  | 87.4 |
|  |  | 45 | 0.836 | 0.334 | 0.506 |  | 88.0 |
|  |  | 73 | 0.836 | 0.344 | 0.496 |  | 86.8 |

TABLE 4

|  | pH | Day | Abs1 | Abs2 | ΔAbs | g/500 ml | g/kg suspension |
|---|---|---|---|---|---|---|---|
| Syrup | 5.13 |  |  |  |  |  |  |
|  |  |  | 0.831 | 0.832 |  |  |  |
|  |  | 0 | 0.830 | 0.354 | 0.477 | 3.00 | 84.6 |
|  |  | 14 | 0.831 | 0.342 | 0.490 | 3.02 | 86.3 |
|  |  | 31 | 0.832 | 0.301 | 0.532 | 3.29 | 86.0 |
|  |  | 45 | 0.830 | 0.307 | 0.524 | 3.24 | 86.1 |
|  |  | 73 | 0.831 | 0.371 | 0.461 | 2.91 | 84.3 |

Results

There was no evidence of breakdown of creatine to creatinine during 73 days' (10.4 weeks') storage at normal room temperature in liquid and solid honey (pH 3.86) and syrup (pH 5.13). There was however a possible small loss of creatine of approximately 5% over the 73 days when suspended in Maxim Energy Gel, pH 2.05.

Creatine monohydrate suspended in Maxim Energy Gel, syrup and liquid honey formed a scum on the surface (i.e. floated to the top) which had to be well mixed in on sampling. This was least with the syrup. No scum was formed with the solid honey which formed a suspension most readily.

Conclusions

When suspended, creatine is stable at room temperature at pHs where it would normally be degraded to creatinine if in solution.

To avoid the unsightly scum being formed it is suggested that creatine is suspended in spreads (such as cheese spread, caviar spread [popular in Scandinavia], smoked fish spread [also popular in Scandinavia—e.g. huckling paste]) contained in tubes. Since usually these are stored at temperatures below ambient (e.g. refrigerated at 4–6° C.) this would further enhance storage.

EXAMPLE 2

This example describes the detailed formulation of an acidic composition in accordance with the invention.

The composition takes the form of a dry powder, which is to be suspended in an edible matrix to constitute a foodstuff comprising creatine and Aloe Vera.

| Ingredients | |
|---|---|
| Dextrose Monohydrate | 300 g |
| Citric Acid | 32 g |
| Pectin (stabilizer) | 6.0 g |
| Salt | 5.0 g |
| Trisodium Citrate | 5.0 g |
| Beta Carotene | 3.0 g |
| Potassium Chloride | 2.9 g |
| Grapefruit Flavor | 2.9 g |
| Tricalcium Phosphate | 2.1 g |
| Heavy Magnesium Carbonate | 2.1 g |
| Vitamin Premix | 1.8 g |
| Lemon Flavor | 1.4 g |
| Orange Flavor | 1.4 g |
| Aspartame | 1.0 g |
| Creatine Monohydrate | 88 g |
| Lyophilized Aloe Vera | 7.6 g |

About 63 g of the above mixture when suspended in 1 liter of matrix provides, per 150 ml serving, about 3 g creatine, 0.6 g Aloe Vera, (equivalent to 120 ml juice), energy kJ 203 (kcal 48, assuming a zero calorie content for the supporting matrix), 11.1 g carbohydrate, 156 mg chloride, 100 mg sodium, 52 mg potassium, 26 mg calcium, 19.5 mg magnesium, 13 mg phosphorus, vitamins (vitamin E 3.4 mg, vitamin C 16.2 mg, Thiamin 0.3 mg, Riboflavin 0.4 mg, Niacin 5.0 mg, vitamin B6 0.4 mg. Folacin 85 $\mu$g, vitamin B12 0.9 $\mu$g, Biotin 0.08 mg and Pantothenic acid 2.2 mg) and traces of protein, fat, and fiber and has a pH of about 3.8.

EXAMPLE 3

This example relates to another embodiment of the invention. The formulation is as in example 2 above, except that the 300 g dextrose monohydrate is omitted and the aspartame content is increased to 2.5 g to compensate. When 5.3 g of this formulation is suspended in 250 ml of matrix, it provides an almost calorie free food (assuming a non-calorific supporting matrix is used) containing creatine and electrolytes which is nutritionally useful to those wishing to lose or maintain their weight.

EXAMPLE 4

The pH of various foodstuffs was analysed, according to the method described in Example 3 above. The results are shown below. Each of these foodstuffs could potentially be used as an edible supporting matrix in a composition in accordance with the invention, by suspending therein a suitable amount of solid creatine. Suitable serving sizes (giving a creatine dose of between 1 and 5 gms creatine) are also indicated.

| Analysis of foodstuffs | pH | Serving (gms) |
|---|---|---|
| Dolmio Sauce for Bolognese (original) | 3.97 | 200 |
| Uncle Ben's Rice Meal Maker | 4.33 | 200 |
| (manufacturer M&M/Mars) | | |
| Sainsbury's economy Coleslaw | 4.22 | 200 |
| Heinz Ravioli in Tomato Sauce | 4.90 | 300 |
| Primula Savoury Spread | 5.80 | 30 |
| Primula Cheese Spread (with chives) | 6.07 | 30 |
| Sainsbury's Tuna and Mayonnaise Spread | 5.80 | 15 |
| Sainsbury's Beef Spread | 6.05 | 15 |

What is claimed is:

1. A composition for human consumption, comprising creatine suspended in an edible supporting matrix wherein said creatine is substantially stable for a period of at least 7 days.

2. A composition according to claim 1, in which the composition has a pH in the range 2.5 to 6.5.

3. A composition according to claim 1, in which the composition has a pH in the range 3.0 to 6.0.

4. A composition according to claim 1, comprising one or more additional components selected from the group consisting of vitamins, lipids, carbohydrates, amino acids, trace elements, colorings, flavors, artificial sweeteners, natural health improving substances, antioxidants, stabilizers, preservatives and buffers.

5. A composition according to claim 1, wherein the edible supporting matrix comprises a spreadable solid.

6. A composition according to claim 1, wherein the edible supporting matrix is selected from the group consisting of: honey, syrup, molasses, treacle and concentrated Aloe Vera gel.

7. A composition according to claim 1, wherein creatine is present in the form of creatine monohydrate or.

8. A composition according to claim 1, wherein a normal serving thereof provides a physiologically effective dose of creatine.

9. An acidic composition according to claim 1, wherein the creatine is substantially stable (with respect to conversion to creatinine) at 20–25° C. for at least 7 days.

10. An acidic composition according to claim 1, wherein the creatine is substantially stable (with respect to conversion to creatinine) at 20–25° C. for at least 31 days.

11. An acidic composition according to claim 1, wherein the creatine is substantially stable (with respect to conversion to creatinine) at 20–25° C. for at least 45 days.

12. An acidic composition according to claim 1, wherein the creatine is substantially stable (with respect to conversion to creatinine) at 20–25° C. for at least 73 days.

13. A method of preparing a creatine containing composition for human consumption in which the creatine is substantially stable, the method comprising the steps of:
providing creatine in solid form;
and mixing the solid creatine with an edible supporting matrix so as to distribute the solid creatine within the supporting matrix.

14. A method of storing creatine in stable form, the method comprising the steps of:
providing creatine in solid form;
mixing the solid creatine with an edible supporting matrix so as to suspend the creatine therein;
and storing the suspended creatine at ambient temperature.

* * * * *